(12) United States Patent
Hogendijk et al.

(10) Patent No.: US 6,908,474 B2
(45) Date of Patent: Jun. 21, 2005

(54) APPARATUS AND METHODS FOR REDUCING EMBOLIZATION DURING TREATMENT OF CAROTID ARTERY DISEASE

(75) Inventors: Michael Hogendijk, Palo Alto, CA (US); Juan Carlos Parodi, Buenos Aires (AR); Mark C. Bates, Charleston, WV (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/100,630

(22) Filed: Mar. 15, 2002

(65) Prior Publication Data

US 2002/0173815 A1 Nov. 21, 2002

Related U.S. Application Data

(63) Continuation-in-part of application No. 09/418,727, filed on Oct. 15, 1999, now Pat. No. 6,423,032, which is a continuation-in-part of application No. 09/333,074, which is a continuation-in-part of application No. PCT/US99/05469, filed on Mar. 12, 1999, now Pat. No. 6,206,868, which is a continuation-in-part of application No. 09/078,263, filed on May 13, 1998, now Pat. No. 6,413,235.

(51) Int. Cl.$^7$ ............................................. A61M 29/00
(52) U.S. Cl. ................................. 606/200; 604/96.01
(58) Field of Search .................... 604/96.01, 103.07, 604/103.08, 108, 508; 606/198, 200

(56) References Cited

U.S. PATENT DOCUMENTS

| | | | |
|---|---|---|---|
| 4,575,371 A | | 3/1986 | Nordqvist et al. |
| 4,577,631 A | * | 3/1986 | Kreamer ..................... 606/108 |
| 4,921,478 A | | 5/1990 | Solano et al. |
| 5,011,488 A | | 4/1991 | Ginsburg |
| 5,102,415 A | | 4/1992 | Guenther et al. |
| 5,499,975 A | | 3/1996 | Cope et al. |
| 5,527,292 A | | 6/1996 | Adams et al. |
| 5,549,626 A | | 8/1996 | Miller et al. |
| 5,569,204 A | | 10/1996 | Cramer |
| 5,794,629 A | | 8/1998 | Frazee |
| 5,833,650 A | | 11/1998 | Imran |
| 5,910,154 A | * | 6/1999 | Tsugita et al. ............... 606/200 |
| 5,911,734 A | * | 6/1999 | Tsugita et al. ............... 606/200 |
| 6,013,085 A | | 1/2000 | Howard |
| 6,029,671 A | | 2/2000 | Stevens et al. |
| 6,161,547 A | | 12/2000 | Barbut |
| 6,206,868 B1 | | 3/2001 | Parodi |
| 6,228,052 B1 | | 5/2001 | Pohndorf |
| 6,295,989 B1 | | 10/2001 | Connors, III |

FOREIGN PATENT DOCUMENTS

EP 0 427 429 A2 5/1991

OTHER PUBLICATIONS

Connors, J.J. and Wojak, J., *Interventional Neuroradiology: Strategies and Practical Techniques*: Chapter 46; Saunders Publishing, Philadelphia, Pennsylvania (1999).

* cited by examiner

Primary Examiner—Kevin C. Simmons
(74) Attorney, Agent, or Firm—Kevin J. Boland

(57) ABSTRACT

Methods and apparatus are provided for removing emboli during an angioplasty, stenting or surgical procedure comprising a catheter having an occlusion element, an aspiration lumen, and a blood outlet port in communication with the lumen, a guide wire having a balloon, a venous return sheath with a blood inlet port, and tubing that couples the blood outlet port to the blood inlet port. Apparatus is also provided for occluding the external carotid artery to prevent reversal of flow into the internal carotid artery. The pressure differential between the artery and the vein provides reverse flow through the artery, thereby flushing emboli. A blood filter may optionally be included in-line with the tubing to filter emboli from blood reperfused into the patient.

26 Claims, 6 Drawing Sheets

APPARATUS AND METHODS FOR REDUCING EMBOLIZATION DURING TREATMENT OF CAROTID ARTERY DISEASE

REFERENCE TO RELATED APPLICATIONS

The present application is a continuation-in-part of U.S. patent application Ser. No. 09/418,727, filed Oct. 15, 1999 now U.S. Pat. No. 6,423,032, which is a continuation-in-part of U.S. patent application Ser. No. 09/333,074, filed Jun. 14, 1999, now U.S. Pat. No. 6,206,868, which is a continuation-in-part of International Application PCT/US99/05469, filed Mar. 12, 1999, which is a continuation-in-part of U.S. patent application Ser. No. 09/078,263, filed May 13, 1998 now U.S. Pat. No. 6,413,235.

FIELD OF THE INVENTION

This invention relates to apparatus and methods for protecting against embolization during vascular interventions, such as carotid artery angioplasty and endarterectomy. More particularly, the apparatus and methods of the present invention induce substantially continuous retrograde flow through the internal carotid artery during treatment during an interventional procedure, without significant blood loss.

BACKGROUND OF THE INVENTION

Carotid artery stenoses typically manifest in the common carotid artery, internal carotid artery or external carotid artery as a pathologic narrowing of the vascular wall, for example, caused by the deposition of plaque, that inhibits normal blood flow. Endarterectomy, an open surgical procedure, traditionally has been used to treat such stenosis of the carotid artery.

An important problem encountered in carotid artery surgery is that emboli may be formed during the course of the procedure, and these emboli can rapidly pass into the cerebral vasculature and cause ischemic stroke.

In view of the trauma and long recuperation times generally associated with open surgical procedures, considerable interest has arisen in the endovascular treatment of carotid artery stenosis. In particular, widespread interest has arisen in transforming interventional techniques developed for treating coronary artery disease, such as angioplasty and stenting, for use in the carotid arteries. Such endovascular treatments, however, are especially prone to the formation of emboli.

Such emboli may be created, for example, when an interventional instrument, such as a guide wire or angioplasty balloon, is forcefully passed into or through the stenosis, as well as after dilatation and deflation of the angioplasty balloon or stent deployment. Because such instruments are advanced into the carotid artery in the same direction as blood flow, emboli generated by operation of the instruments are carried directly to the brain by antegrade blood flow.

Stroke rates after carotid artery stenting have widely varied in different clinical series, from as low as 4.4% to as high as 30%. One review of carotid artery stenting including data from twenty-four major interventional centers in Europe, North America, South America and Asia, had a combined initial failure and combined mortality/stroke rate of more than 7%. Cognitive studies and reports of intellectual changes after carotid artery stenting indicate that embolization is a common event causing subclinical cerebral damage.

Several previously known apparatus and methods attempt to remove emboli formed during endovascular procedures by trapping or suctioning the emboli out of the vessel of interest. These previously known systems, however, provide less than optimal solutions to the problems of effectively removing emboli.

Solano et al. U.S. Pat. No. 4,921,478 describes cerebral angioplasty methods and devices wherein two concentric shafts are coupled at a distal end to a distally-facing funnel-shaped structure. A lumen of the innermost shaft communicates with an opening in the funnel-shaped structure at the distal end, and is open to atmospheric pressure at the proximal end. In use, the funnel-shaped structure is deployed proximally (in the direction of flow) of a stenosis, occluding antegrade flow. An angioplasty balloon catheter is passed through the innermost lumen and into the stenosis, and then inflated to dilate the stenosis. The patent states that when the angioplasty balloon is deflated, a pressure differential between atmospheric pressure and the blood distal to the angioplasty balloon causes a reversal of flow in the vessel that flushes any emboli created by the angioplasty balloon through the lumen of the innermost catheter.

While a seemingly elegant solution to the problem of emboli removal, several drawbacks of the device and methods described in the Solano et al. patent seem to have lead to abandonment of that approach. Chief among these problems is the inability of that system to generate flow reversal during placement of the guide wire and the angioplasty balloon across the stenosis. Because flow reversal does not occur until after deflation of the angioplasty balloon, there is a substantial risk that any emboli created during placement of the angioplasty balloon will travel too far downstream to be captured by the subsequent flow reversal. It is expected that this problem is further compounded because only a relatively small volume of blood is removed by the pressure differential induced after deflation of the angioplasty balloon.

Applicant has determined another drawback of the method described in the Solano patent: deployment of the funnel-shaped structure in the common carotid artery ("CCA") causes reversal of flow from the external carotid artery ("ECA") into the internal carotid artery ("ICA"). Consequently, when a guide wire or interventional instrument is passed across a lesion in either the ECA or ICA, emboli dislodged from the stenosis are introduced into the blood flow and carried into the cerebral vasculature via the ICA.

The insufficient flow drawback identified for the system of the Solano patent is believed to have prevented development of a commercial embodiment of the similar system described in EP Publication No. 0 427 429. EP Publication No. 0 427 429 describes use of a separate balloon to occlude the ECA prior to crossing the lesion in the ICA. However, like Solano, that publication discloses that flow reversal occurs only when the dilatation balloon in the ICA is deflated.

Chapter 46 of *Interventional Neuroradiology: strategies and practical techniques* (J. J. Connors & J. Wojak, 1999), published by Saunders of Philadelphia, Pa., describes using a coaxial balloon angioplasty system for patients having proximal ICA stenoses. In particular, a small, deflated occlusion balloon on a wire is introduced into the origin of the ECA, and a guide catheter with a deflated occlusion balloon is positioned in the CCA just proximal to the origin of the ECA. A dilation catheter is advanced through a lumen of the guide catheter and dilated to disrupt the stenosis. Before deflation of the dilation catheter, the occlusion balloons on the guide catheter and in the ECA are inflated to block antegrade blood flow to the brain. The dilation balloon then is deflated, the dilation catheter is removed, and blood is aspirated from the ICA to remove emboli.

Applicant has determined that cerebral damage still may result from the foregoing previously known procedure, which is similar to that described in EP Publication No. 0 427 429, except that the ICA is occluded prior to the ECA. Consequently, both of these previously known systems and methods suffer from the same drawback—the inability to generate flow reversal at sufficiently high volumes during placement of the guide wire and dilation catheter across the stenosis. Both methods entail a substantial risk that any emboli created during placement of the balloon will travel too far downstream to be captured by the flow reversal.

Applicants note, irrespective of the method of aspiration employed with the method described in the foregoing *Interventional Neuroradiology* article, substantial drawbacks are attendant. If, for example, natural aspiration is used (i.e., induced by the pressure gradient between the atmosphere and the artery), then only a relatively small volume of blood is expected to be removed by the pressure differential induced after deflation of the angioplasty balloon. If, on the other hand, an external pump is utilized, retrieval of these downstream emboli may require a flow rate that cannot be sustained for more than a few seconds, resulting insufficient removal of emboli.

Furthermore, with the dilation balloon in position, the occlusion balloons are not inflated until after inflation of the dilation balloon. Microemboli generated during advancement of the dilation catheter into the stenosed segment may therefore be carried by antegrade blood flow into the brain before dilation, occlusion, and aspiration are even attempted.

Imran U.S. Pat. No. 5,833,650 describes a system for treating stenoses that comprises three concentric shafts. The outermost shaft includes a proximal balloon at its distal end that is deployed proximal of a stenosis to occlude antegrade blood flow. A suction pump then draws suction through a lumen in the outermost shaft to cause a reversal of flow in the vessel while the innermost shaft is passed across the stenosis. Once located distal to the stenosis, a distal balloon on the innermost shaft is deployed to occlude flow distal to the stenosis. Autologous blood taken from a femoral artery using an extracorporeal blood pump is infused through a central lumen of the innermost catheter to provide continued antegrade blood flow distal to the distal balloon. The third concentric shaft, which includes an angioplasty balloon, is then advanced through the annulus between the innermost and outermost catheters to dilate the stenosis.

Like the device of the Solano patent, the device of the Imran patent appears to suffer the drawback of potentially dislodging emboli that are carried into the cerebral vasculature. In particular, once the distal balloon of Imran's innermost shaft is deployed, flow reversal in the vasculature distal to the distal balloon ceases, and the blood perfused through the central lumen of the innermost shaft establishes antegrade flow. Importantly, if emboli are generated during deployment of the distal balloon, those emboli will be carried by the perfused blood directly into the cerebral vasculature, and again pose a risk of ischemic stroke. Moreover, there is some evidence that reperfusion of blood under pressure through a small diameter catheter may contribute to hemolysis and possible dislodgment of emboli.

In applicant's co-pending U.S. patent application Ser. No. 09/333,074, filed Jun. 14, 1999, which is incorporated herein by reference, applicant described the use of external suction to induce regional reversal of flow. That application further described that intermittently induced regional flow reversal overcomes the drawbacks of naturally-aspirated systems such as described hereinabove. However, the use of external suction may in some instances result in flow rates that are too high to be sustained for more than a few seconds. In addition, continuous use of an external pump may result in excessive blood loss, requiring infusion of non-autologous blood and/or saline that causes hemodilution, reduced blood pressure, or raise related safety issues.

In view of these drawbacks of the previously known emboli removal systems, it would be desirable to provide methods and apparatus for removing emboli from within the carotid arteries during interventional procedures, such as angioplasty or carotid stenting, that reduce the risk that emboli are carried into the cerebral vasculature.

It also would be desirable to provide methods and apparatus for removing emboli from within the carotid arteries during interventional procedures, such as angioplasty or carotid stenting, that provide substantially continuous retrograde blood flow from the treatment zone, thereby reducing the risk that emboli are carried into the cerebral vasculature.

It further would be desirable to provide emboli removal methods and apparatus that prevent the development of reverse flow from the ECA and antegrade into the ICA once the CCA has been occluded, thereby enhancing the likelihood that emboli generated by a surgical or interventional procedure are effectively removed from the vessel.

It also would be desirable to provide methods and apparatus that allow for placement of an interventional device so that retrograde flow may be achieved in the treatment vessel prior to having a guide wire cross the lesion.

It also would be desirable to provide methods and apparatus for removing emboli during an angioplasty or carotid stenting procedure that enable filtering of emboli and reduced blood loss.

SUMMARY OF THE INVENTION

In view of the foregoing, it is an object of this invention to provide methods and apparatus for removing emboli from within the carotid arteries during interventional procedures, such as angioplasty or carotid stenting, that reduce the risk that emboli are carried into the cerebral vasculature.

It also is an object of the present invention to provide methods and apparatus for removing emboli from within the carotid arteries during interventional procedures, such as angioplasty or carotid stenting, that provide substantially continuous retrograde blood flow from the treatment zone, thereby reducing the risk that emboli are carried into the cerebral vasculature.

It is another object of the present invention to provide emboli removal methods and apparatus that prevent the development of reverse flow between the ECA and ICA once the common carotid artery has been occluded, thereby enhancing the likelihood that emboli generated by a surgical or interventional procedure are effectively removed from the vessel.

It is still a further object of the present to provide methods and apparatus that allow for placement of an interventional device so that retrograde flow may be achieved in the treatment vessel prior to having a guide wire cross the lesion.

It is yet another object of the present invention to provide methods and apparatus for removing emboli during an angioplasty or carotid stenting procedure that enable filtering of emboli and reduced blood loss.

The foregoing objects of the present invention are accomplished by providing interventional apparatus comprising an arterial catheter, an occlusion element disposed on a guide wire, a venous return sheath, and optionally a blood filter. The arterial catheter has proximal and distal ends, an aspiration lumen extending therethrough, an occlusion element disposed on the distal end, and a hemostatic port and blood outlet port disposed on the proximal end that communicate with the aspiration lumen. The aspiration lumen is sized so that an interventional instrument, e.g., an angioplasty catheter or stent delivery system, may be readily advanced therethrough to the site of a stenosis in either the ECA (proximal to the occlusion element) or the ICA.

In accordance with the principles of the present invention, the arterial catheter is disposed in the CCA proximal of the ICA/ECA bifurcation, the occlusion element on the guide wire is disposed in the ECA to occlude flow reversal from the ECA to the ICA, and the blood outlet port of the arterial catheter is coupled to the venous return sheath, with or without the blood filter disposed therebetween. Higher arterial than venous pressure, especially during diastole, permits substantially continuous flow reversal in the ICA during the procedure (other than when a dilatation balloon is inflated), thereby flushing blood containing emboli from the vessel. The blood is filtered and reperfused into the body through the venous return sheath.

In an alternative embodiment, the occlusion element disposed on the guide wire may be omitted, and replaced with apparatus comprising a self-expanding element having proximal and distal ends, a retrieval wire coupled to the proximal end and an atraumatic tip coupled to the distal end. In this embodiment, a dilator having a lumen may be disposed within the aspiration lumen of the catheter so that the occlusion element is provided in a contracted state within the lumen of the dilator. The occlusion element then is ejected from the dilator and self-expands to occlude the ECA. The dilator then is removed from the aspiration lumen of the catheter, and the distal end of the catheter is re-positioned in the CCA proximal of the carotid bifurcation. Flow reversal is induced in the ICA, as described above, and the self-expanding occlusion element may be contracted using the retrieval wire provided.

BRIEF DESCRIPTION OF THE DRAWINGS

Further features of the invention, its nature and various advantages will be more apparent from the accompanying drawings and the following detailed description of the preferred embodiments, in which.

DESCRIPTION OF THE PREFERRED EMBODIMENTS

Figure 1A:
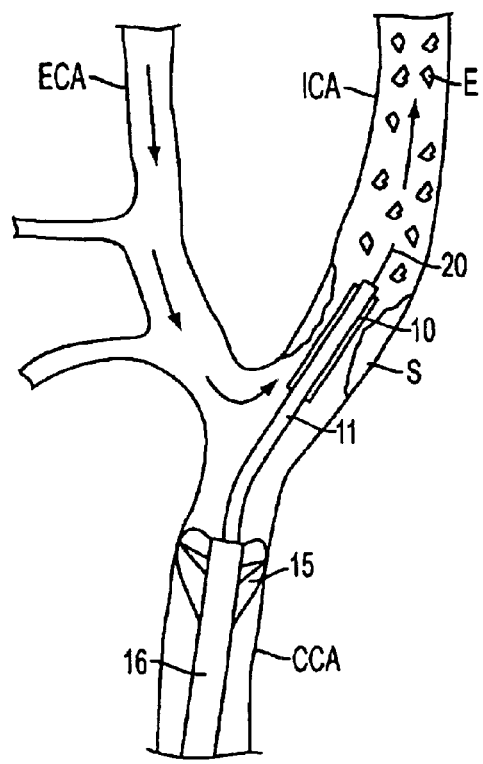
FIGS. 1A and 1B are schematic views of previously known emboli protection systems.
Figure 1B:
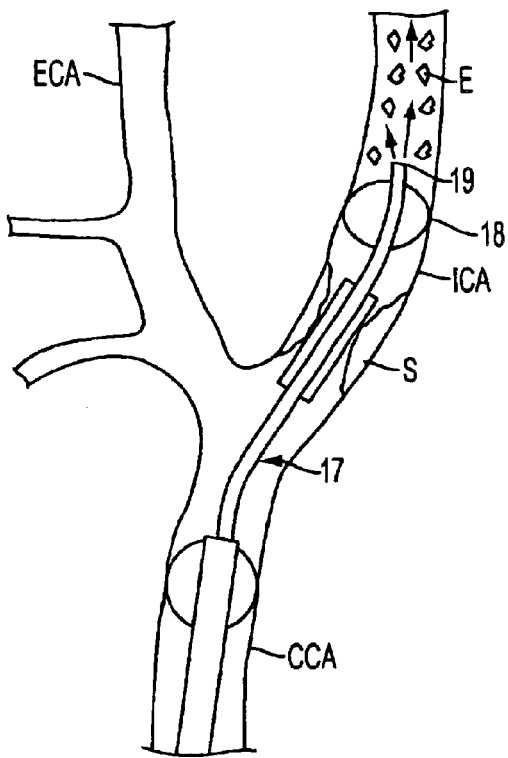

Referring to FIGS. 1A and 1B, drawbacks of previously known emboli removal catheters are described with reference to performing percutaneous angioplasty of stenosis S in common carotid artery CCA.

With respect to FIG. 1A, drawbacks associated with naturally-aspirated emboli removal systems, such as described in the above-mentioned patent to Solano and European Patent Publication, are described. No flow reversal is induced by those systems until after balloon 10 of angioplasty catheter 11 first is passed across the stenosis, inflated, and then deflated. However, applicant has determined that once member 15 of emboli removal catheter 16 is inflated, flow within the ECA reverses and provides antegrade flow into the ICA, due to the lower hemodynamic resistance of the ICA. Consequently, emboli E generated while passing guide wire 20 or catheter 11 across stenosis S may be carried irretrievably into the cerebral vasculature, before flow in the vessel is reversed and directed into the aspiration lumen of emboli removal catheter 16 by opening the proximal end of the aspiration lumen to atmospheric pressure. Furthermore, natural-aspiration may not remove an adequate volume of blood to retrieve even those emboli that have not yet been carried all the way into the cerebral vasculature.

In FIG. 1B, system 17 described in the above-mentioned patent to Imran is shown. As described hereinabove, deployment of distal balloon 18, and ejection of blood out of the distal end of the inner catheter, may dislodge emboli from the vessel wall distal to balloon 18. The introduction of antegrade flow through inner catheter 19 is expected only to exacerbate the problem by pushing the emboli further into the cerebral vasculature. Thus, while the use of positive suction in the Imran system may remove emboli located in the confined treatment field defined by the proximal and distal balloons, such suction is not expected to provide any benefit for emboli dislodged distal of distal balloon 18.

Figure 2:
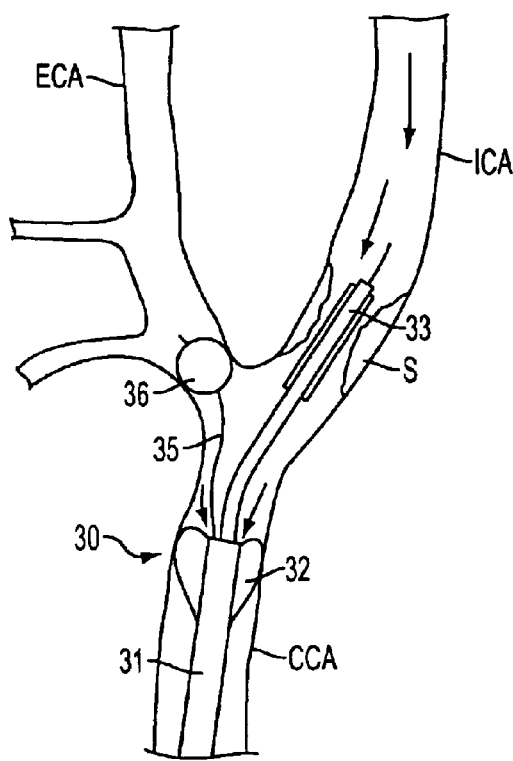
FIG. 2 is a schematic view of an emboli protection system in accordance with principles of the present invention.

Referring now to FIG. 2, apparatus and methods in accordance with the present invention are described. Apparatus 30 comprises catheter 31 having an aspiration lumen and occlusion element 32, and guide wire 35 having inflatable balloon 36 disposed on its distal end. In accordance with the principles of the present invention, antegrade blood flow is stopped when both occlusion element 32 in the CCA and inflatable balloon 36 are deployed. Furthermore, the aspiration lumen of catheter 31 is connected to a venous return sheath (described hereinbelow), disposed, for example, in the patient's femoral vein. In this manner a substantially continuous flow of blood is induced between the treatment site and the patient's venous vasculature. Because flow through the artery is towards catheter 31, any emboli dislodged by advancing a guide wire or angioplasty catheter 33 across stenosis S causes the emboli to be aspirated by catheter 31.

Unlike the previously known naturally-aspirated systems, the present invention provides substantially continuous retrograde blood flow through the ICA while preventing blood from flowing retrograde in the ECA and antegrade into the ICA, thereby preventing emboli from being carried into the cerebral vasculature. Because the apparatus and methods of the present invention "recycle" emboli-laden blood from the arterial catheter through the blood filter and to the venous return sheath, the patient experiences significantly less blood loss.

Figure 3A:
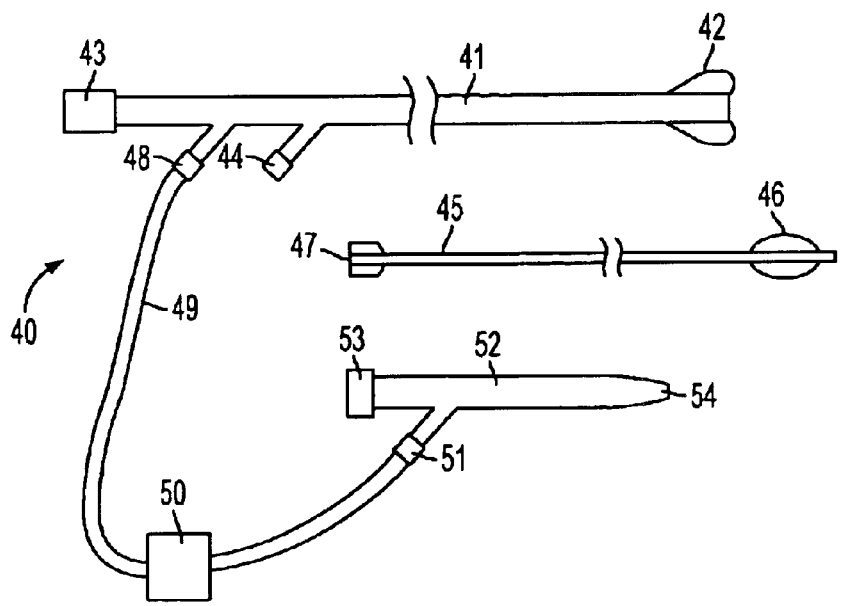
FIGS. 3A–3D are, respectively, a schematic view of apparatus in accordance with a first embodiment of the present invention, detailed side and sectional views of the distal end of an interventional device of the present invention, and a cross-sectional view of an interventional device of the present invention.

Referring now to FIG. 3A, embolic protection apparatus 40 constructed in accordance with the principles of the present invention is described. Apparatus 40 comprises arterial catheter 41, guide wire 45, venous return sheath 52, tubing 49 and optional blood filter 50.

Catheter 41 includes distal occlusion element 42, proximal hemostatic port 43, e.g., a Touhy-Borst connector, inflation port 44, and blood outlet port 48. Guide wire 45 includes balloon 46 that is inflated via inflation port 47. Tubing 49 couples blood outlet port 48 to filter 50 and blood inlet port 51 of venous return sheath 52.

Guide wire 45 and balloon 46 are configured to pass through hemostatic port 43 and the aspiration lumen of catheter 41 (see FIGS. 3C and 3D), so that the balloon may be advanced into and occlude the ECA. Port 43 and the aspiration lumen of catheter 41 are sized to permit additional interventional devices, such as angioplasty balloon catheters, atherectomy devices and stent delivery systems to be advanced through the aspiration lumen when guide wire 45 is deployed.

Guide wire 45 preferably comprises a small diameter flexible shaft having an inflation lumen that couples inflatable balloon 46 to inflation port 47. Inflatable balloon 46 preferably comprises a compliant material, such as described hereinbelow with respect to occlusion element 42 of emboli removal catheter 41.

Venous return sheath 52 includes hemostatic port 53, blood inlet port 51 and a lumen that communicates with ports 53 and 51 and tip 54. Venous return sheath 52 may be constructed in a manner per se known for venous introducer catheters. Tubing 49 may comprise a suitable length of a biocompatible material, such as silicone. Alternatively, tubing 49 may be omitted and blood outlet port 48 of catheter 41 and blood inlet port 51 of venous return sheath 52 may be lengthened to engage either end of filter 50 or each other.

Figure 3B:
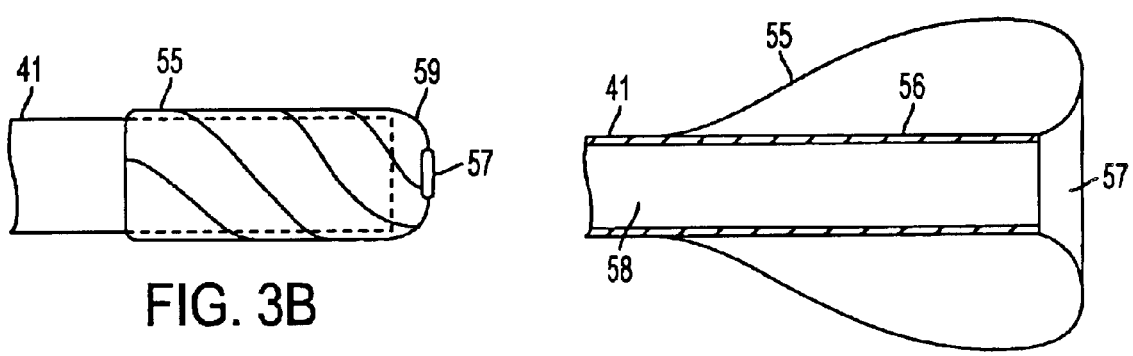
Figure 3C:
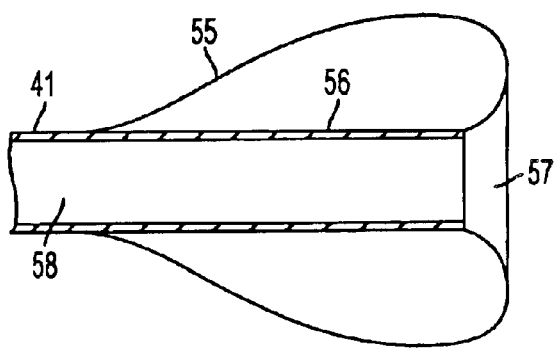

With respect to FIGS. 3B and 3C, distal occlusion element 42 comprises expandable bell or pear-shaped balloon 55. In accordance with manufacturing techniques that are known in the art, balloon 55 comprises a compliant material, such as polyurethane, latex or polyisoprene which has variable thickness along its length to provide a bell-shape when inflated. Balloon 55 is affixed to distal end 56 of catheter 41, for example, by gluing or a melt-bond, so that opening 57 in balloon 55 leads into aspiration lumen 58 of catheter 41. Balloon 55 preferably is wrapped and heat treated during manufacture so that distal portion 59 of the balloon extends beyond the distal end of catheter 41 and provides an atraumatic tip or bumper for the catheter.

Figure 3D:
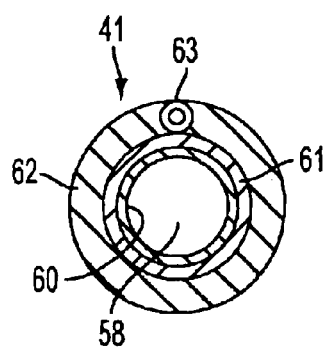

As shown in FIG. 3D, catheter 41 preferably comprises inner layer 60 of low-friction material, such as polytetrafluoroethylene ("PTFE"), covered with a layer of flat stainless steel wire braid 61 and polymer cover 62 (e.g., polyurethane, polyethylene, or PEBAX). Inflation lumen 63 is disposed within polymer cover 62 and couples inflation port 44 to balloon 55. In a preferred embodiment of catheter 41, the diameter of lumen 58 is about 7 Fr, and the outer diameter of the catheter is about 9 Fr.

Figure 4A:
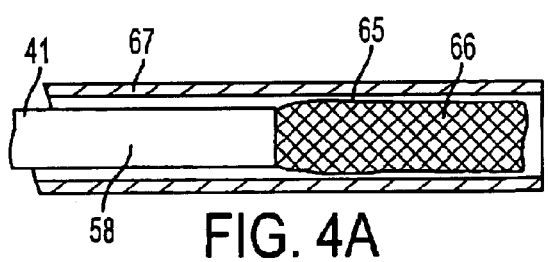
FIGS. 4A and 4B are views of the distal end of an alternative interventional device suitable for use in the system of the present invention.
Figure 4B:
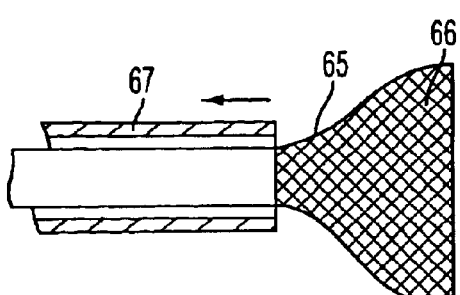

Referring now to FIGS. 4A and 4B, an alternative embodiment of occlusion element 42 of the system of FIG. 3A is described. In FIGS. 4A and 4B, occlusion element 42 of emboli removal catheter 41 comprises self-expanding wire basket 65 covered with elastomeric polymer 66, such as latex, polyurethane or polyisoprene. Alternatively, a tightly knit self-expanding wire mesh may be used, with or without an elastomeric covering.

Catheter 41 is contained within movable sheath 67. Catheter 41 is inserted transluminally with sheath 67 in a distalmost position, and after basket 65 has been determined to be in a desired position proximal to a stenosis, sheath 67 is retracted proximally to cause basket 65 to deploy. Upon completion of the procedure, basket 65 is again collapsed within sheath 67 by moving the sheath to its distalmost position. Operation of the system of FIG. 3A using the emboli removal catheter of FIGS. 4A and 4B is similar to that described hereinbelow for FIGS. 5A–5D, except that the occlusion element self-expands when sheath 67 is retracted, rather than by infusing an inflation medium to balloon 55.

Figure 5A:
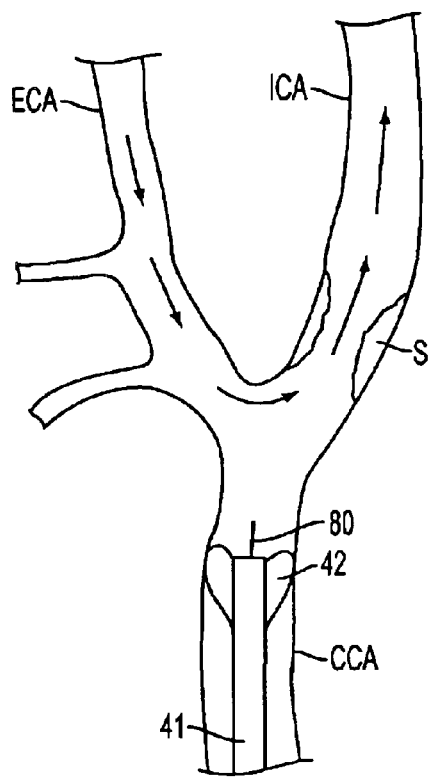
FIGS. 5A–5D illustrate a method of using the system of FIG. 3 in accordance with the principles of the present invention.

Referring now to FIGS. 5A–5D, use of the apparatus of FIG. 3 in accordance with the methods of the present invention is described. In FIG. 5, stenosis S is located in internal carotid artery ICA above the bifurcation between the ICA and the external carotid artery ECA. In a first step, guide wire 80 is inserted into a patient's arterial vasculature and a distal end of guide wire 80 preferably is disposed just proximal of the carotid bifurcation, as shown in FIG. 5A. A dilator (not shown), which is disposed within catheter 41, then may be inserted over guide wire 80 to advance catheter 41 to a position proximal of stenosis S, as shown in FIG. 5A, and the dilator may be removed. Balloon 55 of distal occlusion element 42 then is inflated via inflation port 44, preferably using a radiopaque contrast solution, and guide wire 80 may be removed. Once balloon 55 of distal occlusion element 42 is inflated, flow within the ECA reverses and provides antegrade flow into the ICA, as shown in FIG. 5A, due to the lower hemodynamic resistance of the ICA.

Venous return sheath 52 then is introduced into the patient's femoral vein, either percutaneously or via a surgical cut-down. Filter 50 then is coupled between blood outlet port 48 of catheter 41 and blood inlet port 51 of venous return sheath 52 using tubing 49, and any air is removed from the line. Once this circuit is closed, negative pressure in the venous sheath during diastole will establish a low rate continuous flow of blood through aspiration lumen 58 of catheter 41, to the patient's vein via venous return sheath 52.

Figure 5B:
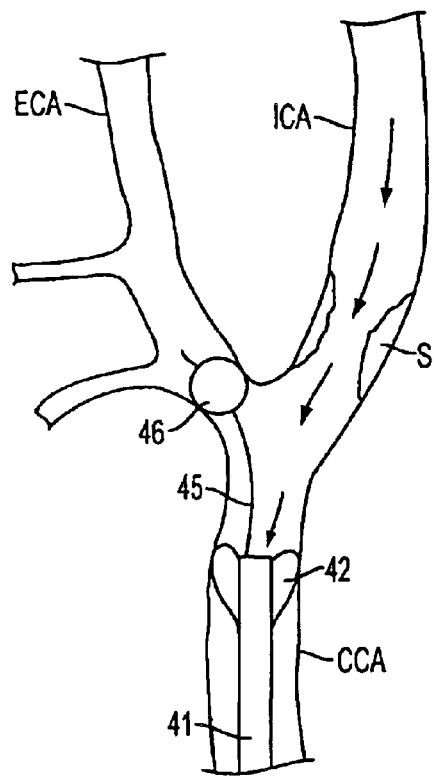

Guide wire 45 and balloon 46 then may be advanced through aspiration lumen 58. When balloon 46 is disposed within the ECA, as determined, e.g., using a fluoroscope and a radiopaque inflation medium injected into balloon 46, balloon 46 is inflated. The deployment of balloon 46 in the ECA, in conjunction with the negative pressure in the venous sheath during diastole, will established a retrograde flow dynamic in the ICA, as shown in FIG. 5B.

This continuous retrograde flow in the ICA due to the difference between venous pressure and arterial pressure will continue throughout the interventional procedure. Specifically, blood passes through aspiration lumen 58 and blood outlet port 48 of catheter 41, through biocompatible tubing 49 to filter 50, and into blood inlet port 51 of venous return sheath 52, where it is reperfused into the remote vein. Filtered emboli collect in filter 50 and may be studied and characterized upon completion of the procedure.

Continuous blood flow (except during inflation of any dilatation instruments) with reperfusion in accordance with the present invention provides efficient emboli removal with significantly reduced blood loss. Alternatively, filter 50 may be omitted, in which case emboli removed from the arterial side will be introduced into the venous side, and eventually captured in the lungs. Because of a low incidence of septal defects, which could permit such emboli to cross-over to the left ventricle, the use of filter 50 is preferred.

Figure 5C:
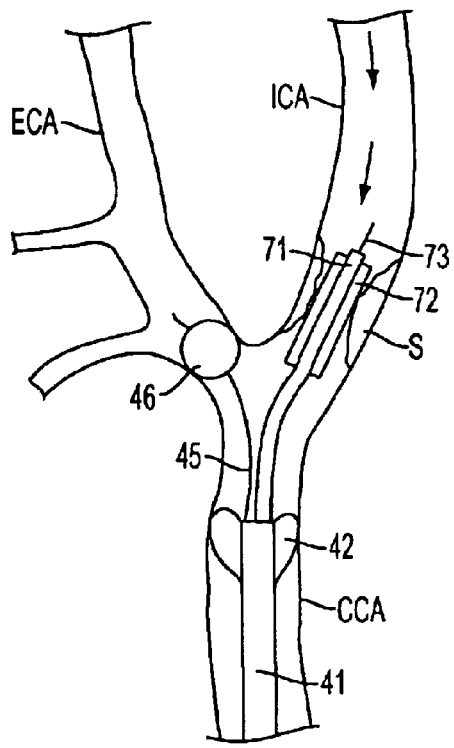

Referring to FIG. 5C, an interventional instrument, such as conventional angioplasty balloon catheter 71 having balloon 72, is loaded through hemostatic port 43 and aspiration lumen 58 and positioned within the stenosis, preferably via guide wire 73. Hemostatic port 43 is closed and instrument 71 is actuated to disrupt the plaque forming stenosis S.

Figure 5D:
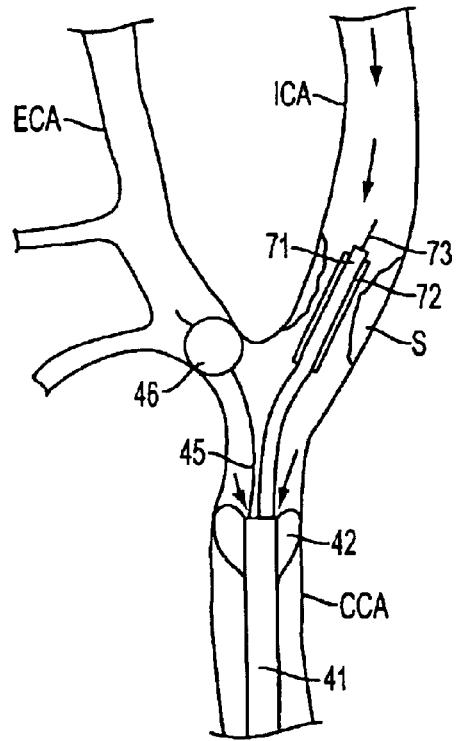

As seen in FIG. 5D, upon completion of the angioplasty portion of the procedure using catheter 71, balloon 72 is deflated. Throughout the procedure, except when the dilatation balloon is fully inflated, the pressure differential between the blood in the ICA and the venous pressure causes blood in the ICA to flow in a retrograde direction into aspiration lumen 58 of emboli removal catheter 41, thereby flushing any emboli from the vessel. The blood is filtered and reperfused into the patient's vein.

As set forth above, the method of the present invention protects against embolization, first, by preventing the reversal of blood flow from the ECA to the ICA when distal occlusion element 42 is inflated, and second, by providing continuous, low volume blood flow from the carotid artery to the remote vein in order to filter and flush any emboli from the vessel and blood stream. Advantageously, the method of the present invention permits emboli to be removed with little blood loss, because the blood is filtered and reperfused into the patient. Furthermore, continuous removal of blood containing emboli prevents emboli from migrating too far downstream for aspiration.

Figure 6A:
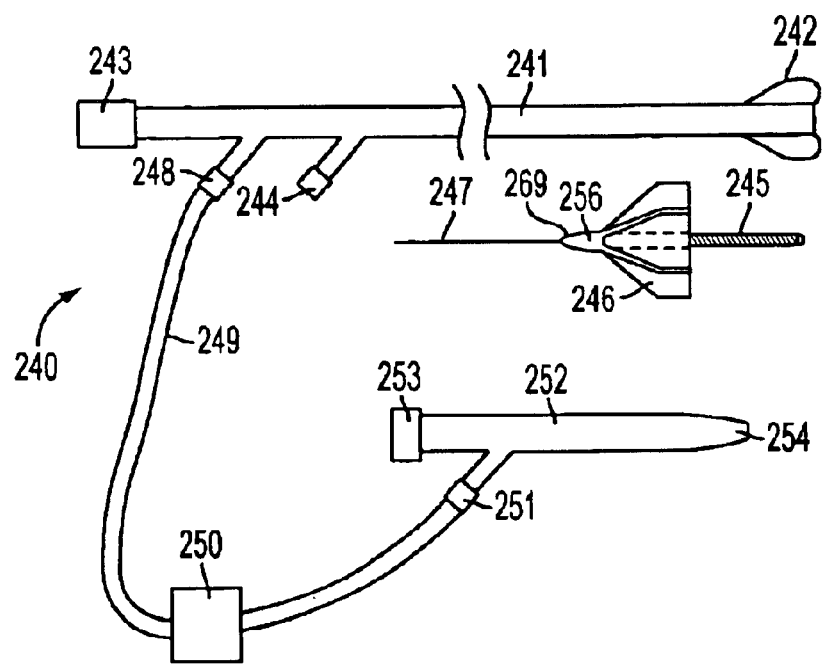
FIGS. 6A–6C are, respectively, a schematic view and cross-sectional views of the proximal and distal ends of a catheter of an alternative embodiment of the present invention.
Figure 6B:
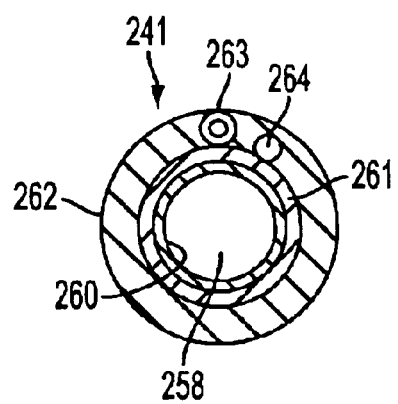

Referring now to FIG. 6, apparatus 240 constructed in accordance with the present invention is described. Apparatus 240 is an alternative embodiment of apparatus 40 described hereinabove and comprises arterial catheter 241 having proximal and distal ends, distal occlusion element 242 disposed on the distal end, proximal hemostatic port 243, inflation port 244 and blood outlet port 248. Self-expanding occlusion element 246 having proximal and distal ends preferably comprises non-expanding occlusion base 256 disposed at the proximal end, wherein occlusion base 256 comprises proximal taper 269. Occlusion element 246 is coupled to retrieval wire 247 at the proximal end and atraumatic tip 245 at the distal end, e.g., by affixing retrieval wire 247 to proximal taper 269 of occlusion base 256 and affixing atraumatic tip 245 to a distal end of occlusion base 256, as shown in FIG. 6A. Biocompatible tubing 249 couples blood outlet port 248 to filter 250 and to blood inlet port 251 of venous return sheath 252. Arterial catheter 241, venous return sheath 252 and tubing 249 are constructed as described hereinabove, except as noted below.

Figure 6C:
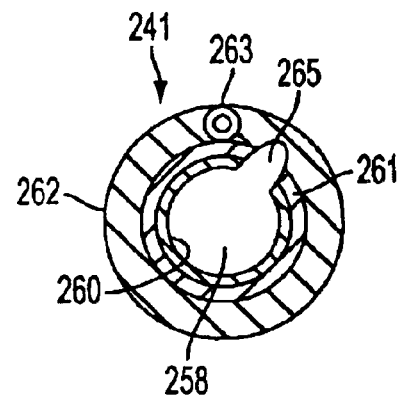

Catheter 241 comprises aspiration lumen 258, as shown in FIG. GB, which is sized to permit interventional devices, such as angioplasty balloon catheters, atherectomy devices and stent delivery systems to be advanced through port 243 and the aspiration lumen. Retrieval wire lumen 264 is sized to permit longitudinal movement of retrieval wire 247 of occlusion element 246. Retrieval wire lumen 264 spans from the proximal end of catheter 241 to a location just proximal of the distal end, e.g., about 1 to 2 cm proximal of the distal end of catheter 241. At this location, retrieval wire lumen 264 merges with aspiration lumen 258 to form channel 265, as shown in FIG. 6C.

Figure 7A:
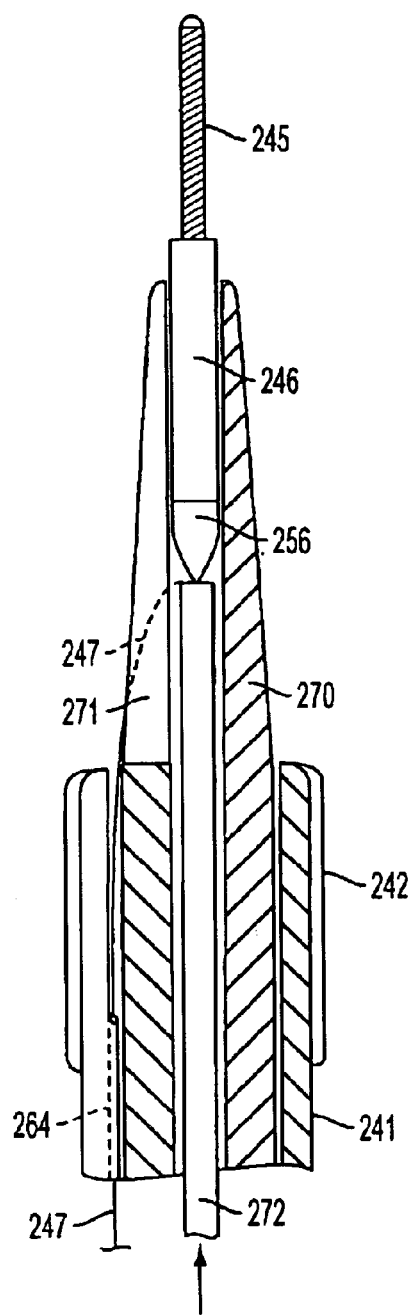
FIGS. 7A–7B depict features of the self-expanding occlusion element of FIGS. 6.

Referring to FIG. 7, deployment of occlusion element 246 is described. Occlusion element 246 initially is provided in a contracted state, as shown in FIG. 7A. In the contracted state, occlusion element 246 is disposed within a lumen of dilator 270, which in turn is disposed within aspiration lumen 258 of catheter 241. Dilator 270 comprises proximal and distal ends, with occlusion element 246 being positioned within a slot in the distal end. The distal end of dilator 270 tapers and extends distal to catheter 241, as shown in FIG. 7A. Atraumatic tip 245 of occlusion element 246 extends distal to dilator 270 and facilitates guidance of the device through a patient's vasculature.

Push member 272 having proximal and distal ends is configured for longitudinal movement within the lumen of dilator 270. During delivery of catheter 241, the distal end of push member 272 preferably abuts occlusion base 256 of occlusion element 246, while the proximal end of push member 272 may be manipulated by a physician. Dilator 270 comprises slot 271 disposed at the distal end. Slot 271 allows retrieval wire 247 to extend from a distal point in which it is coupled to occlusion base 256, to a proximal point in which it enters retrieval wire lumen 264, as shown in FIG. 7A.

Figure 7B:
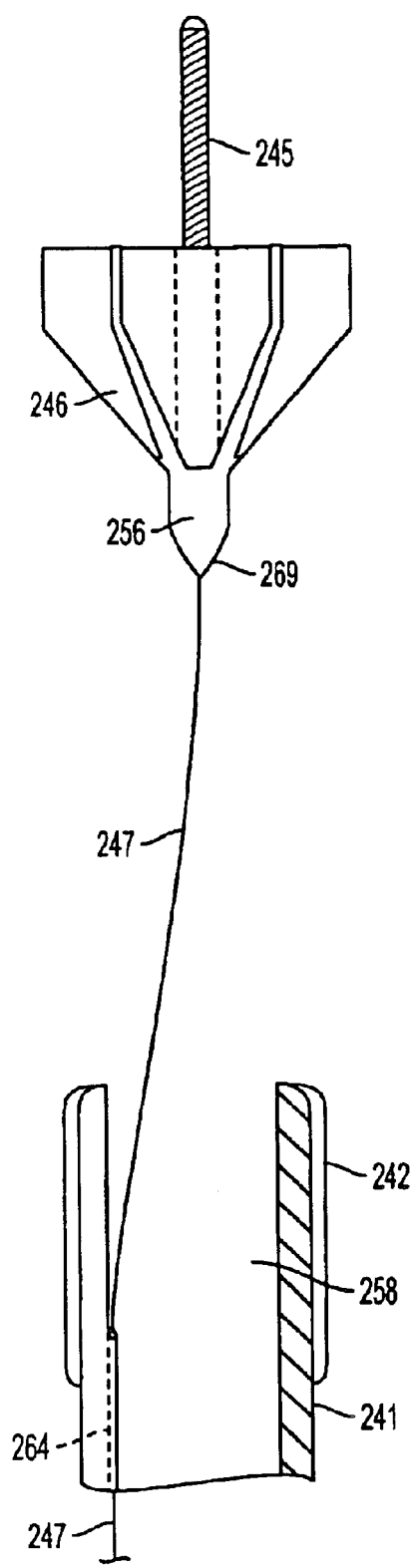

Upon positioning the distal end of catheter 241 at a selected location, push member 272 is held stationary while dilator 270 is retracted proximally, so that occlusion element 246 effectively is no longer constrained within the lumen of dilator 270. This causes occlusion element 246 to self-expand to a predetermined shape, as shown in FIG. 7B. Occlusion element 246 is sized to occlude flow in the external carotid artery in this deployed state.

Dilator slot 271 allows retrieval wire 247 to move freely during the deployment of occlusion element 246. After deployment of occlusion element 246, dilator 270 and push member 272 are removed from within aspiration lumen 258, as shown in FIG. 7B. Catheter 241 then may be positioned separately from occlusion element 246, as described hereinbelow with respect to FIG. 8, and may be used to deliver other interventional apparatus, such as angioplasty catheters or stent delivery systems.

At the completion of the interventional procedure, occlusion element 246 is contracted by proximally retracting retrieval wire 247. Occlusion element 246 is retrieved when the proximal load exerted on retrieval wire 247 exceeds the frictional forces between occlusion element 246 and the external carotid artery wall. After occlusion element 246 is contracted, occlusion base 256, occlusion element 246 and atraumatic tip 245 may be retracted partially or fully into aspiration lumen 258. Channel 265 of FIG. 6C may be used to provide a transition at the distal end of catheter 241 so that occlusion element 246 is effectively guided into aspiration lumen 258 when retrieval wire 247 is retracted proximally. In effect, this allows occlusion element 246 to be contained within at least a distal portion of catheter 241, to allow for safe removal of catheter 241.

Referring to FIG. 8, method steps for using the apparatus of FIGS. 6–7 to treat carotid artery disease is provided. In FIG. 8, stenosis S is located in the ICA above the carotid bifurcation. In a first step, catheter 241 is inserted, either percutaneously and transluminally or via a surgical cut-down, to a position proximal of stenosis S. Occlusion element 246 is disposed within a lumen at the distal end of dilator 270, as described in FIG. 7A, and atraumatic tip 245 is used to guide catheter 241. The distal end of catheter 241 preferably is positioned within the ECA, as shown in FIG. 8A, so that occlusion element 246 will be deployed into the ECA.

Figure 8A:
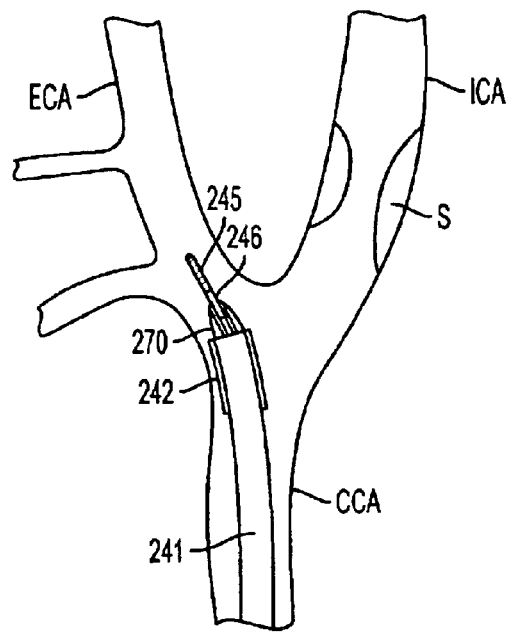
FIGS. 8A–8D illustrate a method of using the system of FIGS. 6 in accordance with the principles of the present invention.
Figure 8B:
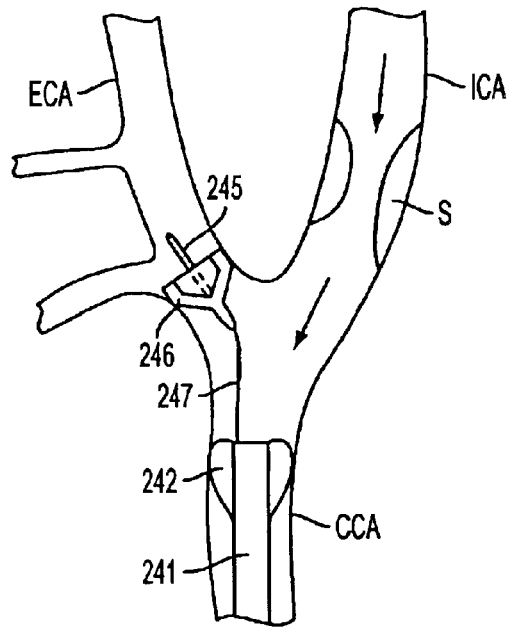

Push member 272 of FIG. 7A then is held stationary while dilator 270 is retracted proximally, so that occlusion element 246 is no longer constrained by dilator 270. Occlusion element 246 then self-expands to occlude flow in the ECA, as shown in FIG. 8B. Dilator 270 and push member 272 then are removed from within aspiration lumen 258, and catheter 241 is retracted to a location just proximal of the carotid bifurcation, as shown in FIG. 8B. Distal occlusion element 242 of catheter 241 then may be inflated via inflation port 244 to occlude antegrade flow in the CCA.

Venous return sheath 252 may be introduced into the patient's femoral vein, either percutaneously or via a surgical cut-down, and filter 250 may be coupled between blood outlet port 248 of catheter 241 and blood inlet port 251 of venous return sheath 252 using tubing 249. Once this circuit is closed, negative pressure in the venous sheath establishes a continuous retrograde flow of blood through aspiration lumen 258 of catheter 241, as shown in FIG. 8B, to the patient's vein via venous return sheath 252. Alternatively, venous return sheath 252 may be omitted, and the proximal end of catheter 241 connected to a receptacle to collect blood aspirated through aspiration lumen 258.

Figure 8C:
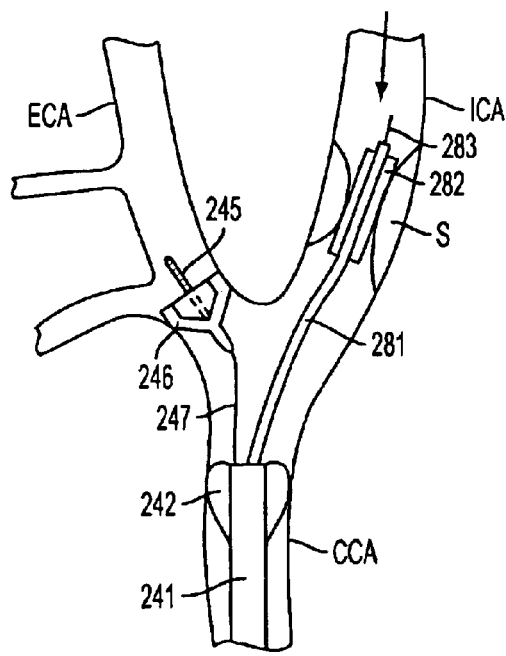

Referring to FIG. 8C, with distal occlusion element 242 inflated and a retrograde flow established in the ICA, an interventional instrument, such as conventional angioplasty balloon catheter 281 having balloon 282, is loaded through hemostatic port 243 and aspiration lumen 258 and positioned within stenosis S, preferably via guide wire 283. Hemostatic port 243 is closed and instrument 281 is actuated to disrupt stenosis S.

Figure 8D:
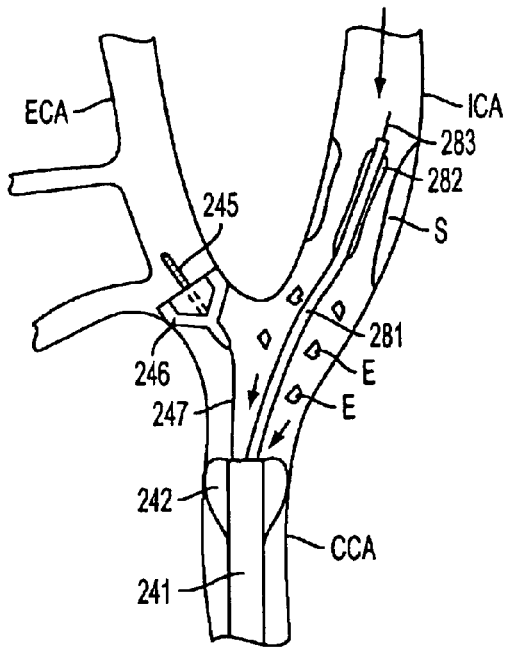

As shown in FIG. 8D, upon completion of the angioplasty portion of the procedure using catheter 281, balloon 282 is deflated. Throughout the procedure, except when the dilatation balloon is fully inflated, the pressure differential between the blood in the ICA and the venous pressure causes blood in the ICA to flow in a retrograde direction and into aspiration lumen 258 of emboli removal catheter 241, thereby flushing any emboli E from the vessel.

Upon satisfactory removal of emboli, occlusion element 246 is contracted by proximally retracting retrieval wire 247. Occlusion element 246 still further may be contracted when it contacts the distal end of catheter 241. When occlusion element 246 has been contracted, it then may be retracted either partially or fully into aspiration lumen 258 of catheter 241 via channel 265. Distal occlusion element 242 of catheter 241 then is deflated and the apparatus is removed from the patient's vessel.

While preferred illustrative embodiments of the invention are described above, it will be apparent to one skilled in the art that various changes and modifications may be made. The appended claims are intended to cover all such changes and modifications that fall within the true spirit and scope of the invention.

What is claimed is:

1. Apparatus for removing emboli during an angioplasty or stenting procedure from a vessel having a trunk portion coupled to first and second branches via a bifurcation, the apparatus comprising:
   a catheter having proximal and distal ends, a first lumen extending therethrough, a blood outlet port in communication with the first lumen, and a distal occlusion element disposed on the distal end of the catheter, the catheter adapted to be disposed in a patient's trunk portion proximal to the bifurcation; and
   an occlusion member having proximal and distal ends, the occlusion member comprising a self-expanding blood impermeable element, a retrieval wire coupled to the proximal end of the occlusion member and an atraumatic tip coupled to the distal end of the occlusion member, wherein the occlusion member further comprises a contracted state and a deployed state in which the self expanding blood impermeable element is configured to substantially prevent flow in one of the first and second branch vessels.

2. The apparatus of claim 1 wherein the occlusion member is configured to occlude flow in an external carotid artery in the deployed state.

3. The apparatus of claim 1 wherein the distal occlusion element is an inflatable member.

4. The apparatus of claim 1 further comprising:
   a venous return sheath having proximal and distal ends, a lumen extending therethrough, and a blood inlet port in communication with the lumen; and
   tubing that couples the blood outlet port of the catheter to the blood inlet port of the venous return sheath.

5. The apparatus of claim 4 further comprising a blood filter disposed between the blood outlet port of the catheter and the blood inlet port of the venous return sheath.

6. The apparatus of claim 1 further comprising a dilator having proximal and distal ends and a lumen extending therethrough, wherein the dilator is configured to be disposed within the first lumen of the catheter.

7. The apparatus of claim 6 wherein the occlusion member is adapted to be disposed within the lumen of the dilator in the contracted state.

8. The apparatus of claim 6 wherein the dilator comprises a slot at the distal end that is configured to permit movement of the retrieval wire within the slot.

9. The apparatus of claim 6 further comprising a push member having proximal and distal ends, wherein the push member is configured for longitudinal movement within the lumen of the dilator.

10. The apparatus of claim 9 wherein the distal end of the push member configured to abut the proximal end of the occlusion member within the lumen of the dilator.

11. The apparatus of claim 1 wherein the proximal end of the occlusion member comprises a taper.

12. The apparatus of claim 1 further comprising a second lumen, wherein the retrieval wire is configured for longitudinal movement within the second lumen.

13. The apparatus of claim 12 wherein the second lumen merges with the first lumen along a portion of the distal end of the catheter.

14. Apparatus for removing emboli from a carotid artery during an angioplasty or stenting procedure, the apparatus comprising:
   a catheter having proximal and distal ends, a first lumen extending therethrough, a blood outlet port in communication with the first lumen, and a distal occlusion element disposed on the distal end of the catheter, the catheter adapted to be disposed in a patient's common carotid artery; and
   an occlusion member having proximal and distal ends, the occlusion member comprising a plurality of self-expanding struts carrying a blood impermeable element, a retrieval wire coupled to the proximal end of the occlusion member and an atraumatic tip coupled to the distal end of the occlusion member, wherein the occlusion member further comprises a contracted state and a deployed state in which the self-expanding blood impermeable element is configured to substantially prevent flow in one of either an internal carotid artery or an external carotid artery.

15. The apparatus of claim 14 wherein the occlusion member is configured to occlude flow in an external carotid artery in the deployed state.

16. The apparatus of claim 14 wherein the distal occlusion element is an inflatable member.

17. The apparatus of claim 14 further comprising:
a venous return sheath having proximal and distal ends, a lumen extending therethrough, and a blood inlet port in communication with the lumen, and
tubing that couples the blood outlet port of the catheter to the blood inlet port of the venous return sheath.

18. The apparatus of claim 17 further comprising a blood filter disposed between the blood outlet port of the catheter and the blood inlet port of the venous return sheath.

19. The apparatus of claim 14 further comprising a dilator having proximal and distal ends and a lumen extending therethrough, wherein the dilator is configured to be disposed within the first lumen of the catheter.

20. The apparatus of claim 19 wherein the occlusion member is adapted to be disposed within the lumen of the dilator in the contracted state.

21. The apparatus of claim 19 wherein the dilator comprises a slot at the distal end that is configured to permit movement of the retrieval wire within the slot.

22. The apparatus of claim 19 further comprising a push member having proximal and distal ends, wherein the push member is configured for longitudinal movement within the lumen of the dilator.

23. The apparatus of claim 22 wherein the distal end of the push member is configured to abut the proximal end of the occlusion member within the lumen of the dilator.

24. The apparatus claim 14 wherein the proximal end of the occlusion member comprises a taper.

25. The apparatus of claim 14 further comprising a second lumen, wherein the retrieval wire is configured for longitudinal movement within the second lumen.

26. The apparatus of claim 25 wherein the second lumen merges with the first lumen along a portion of the distal end of the catheter.

* * * * *